United States Patent
De Jong et al.

(10) Patent No.: US 6,909,022 B2
(45) Date of Patent: Jun. 21, 2005

(54) PROCESS OF REMOVING ORGANIC HALOGEN-CONTAINING COMPOUNDS

(75) Inventors: Feike De Jong, Amsterdam (NL); Johannes Jacobus Maria Snel, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/845,933

(22) Filed: May 14, 2004

(65) Prior Publication Data

US 2004/0267060 A1 Dec. 30, 2004

(30) Foreign Application Priority Data

May 14, 2003 (EP) .......................................... 03253007

(51) Int. Cl.$^7$ .......................... C07C 27/26; C07C 29/74; C07C 29/76
(52) U.S. Cl. ....................... 568/872; 568/868; 568/869; 568/870; 549/541; 549/542
(58) Field of Search ................................ 549/541, 542; 568/868, 869, 870, 872

(56) References Cited

U.S. PATENT DOCUMENTS

| | | | |
|---|---|---|---|
| 4,547,620 A | 10/1985 | Miyata et al. | 585/852 |
| 5,405,977 A | 4/1995 | Cuscurida et al. | 549/541 |
| 5,510,499 A | 4/1996 | Mendoza-Frohn et al. | 549/229 |
| 6,437,199 B1 | 8/2002 | Oka et al. | 568/867 |

FOREIGN PATENT DOCUMENTS

| | | |
|---|---|---|
| GB | 1177877 | 1/1970 |
| GB | 1314607 | 4/1973 |
| JP | A-06238165 | 8/1994 |

OTHER PUBLICATIONS

H.D. Cowan et al, A Kinetic Study of the Neutral Hydrolysis of Ethylene Fluoro–, Bromo–, and Iodohydrin, J. Am. Chem. Soc., 1950, 72, 1194.
Ulmann's Ency. Of Industrial Chem., 5$^{th}$ Ed., 1989, vol. A14, pp. 422–440.
Kirk–Othmer, Ency. Of Chem. Technology, 4$^{th}$ Ed., 1995, vol. 14, p. 737.
H. Schaper et al, Appliefd Catalysis, 54, (1989), 79–90.
Watanabe, Y. et al, Microporous and Mesoporous Materials 22 (1998) 399–407.
Kirk–Othmer, Ency. Of Chem. Technology, 4$^{th}$ Ed., 1995, vol. 14, pp. 740–741.
Kirk–Othmer, Ency. of Chem. Technology, 4$^{th}$ Ed., vol. 12, pp. 700–725.
CRC Handbook of Chemistry and Physics, 72nd Ed., 1991, pp. 1–11.
International Search Report, dated Aug. 4, 2004.

*Primary Examiner*—Elvis O. Price

(57) ABSTRACT

The present invention relates to a process of removing organic halogen-containing compounds from a liquid stream mainly containing one or more of the compounds selected from the group consisting of glycol, water and alcohol, which process involves contacting the stream with an ion-exchange material containing basic anions selected from the group of hydroxide, carbonate and bicarbonate.

16 Claims, No Drawings

PROCESS OF REMOVING ORGANIC HALOGEN-CONTAINING COMPOUNDS

FIELD OF THE INVENTION

The invention relates to a process for the removal of organic halogen-containing compounds from a liquid stream.

BACKGROUND OF THE INVENTION

The production process for glycols as described for instance in Kirk-Othmer, Encyclopedia of Chemical Technology, 4$^{th}$ Edition, Volume 12, pages 700 to 725, is a widely applied process. In such a process, monoethylene glycol or monopropylene glycol along with di- and triethylene glycol, or di- and tripropylene glycol (all of which are further referred to as glycols) are obtained by direct hydrolysis of the corresponding alkylene oxides. The process has the disadvantage of requiring a large excess of water for the reaction with alkylene oxides. Due to this excess the process consumes much energy. Furthermore, the process also has a limited efficiency due to the significant amount of undesired side products formed. A different process for production of glycols from alkylene oxides, which requires much less water and therefore has a lower energy requirement and a higher efficiency, is the reaction of alkylene oxide with carbon dioxide to obtain the corresponding alkylene carbonate, and the subsequent catalytic hydrolysis reaction with water or catalytic transesterification with alcohol to obtain the corresponding glycol.

The present invention pertains to the removal of organic halogen-containing compounds from streams containing one or more of glycol, water and alcohol.

Such streams can be produced by a process involving the steps of (a) reacting an alkylene oxide with carbon dioxide in the presence of a halide-containing catalyst to obtain a reaction mixture containing the corresponding alkylene carbonate, and (b) contacting the reaction mixture obtained in step (a) with water and/or alcohol in the presence of a suitable catalyst to obtain a reaction mixture containing glycol.

A disadvantage of the use of halide-containing catalysts in step (a) is that their presence also leads to formation of organic halogen-containing compounds.

U.S. Pat. No. 5,405,977 describes the removal of halogen-containing compounds from alkylene carbonates produced according to step (a) with the help of a halide-containing catalyst by contacting the contaminated alkylene carbonate with hydrotalcite under non-aqueous conditions. In the process described in U.S. Pat. No. 5,405,977, alkylene carbonate is prepared and then separated from the initial reaction mixture, for instance by one or more vacuum distillation steps prior to removal of the halogen-containing compounds.

Although the process described in this document represents a viable way to purify alkylene carbonates contaminated by halogen-containing compounds, there are several disadvantages associated with the process.

The required non-aqueous conditions make the process itself cumbersome to perform on an industrial scale, as all components need to be essentially water-free.

Furthermore, under conditions suitable for distillation of alkylene carbonates, part of the alkylene carbonate decomposes to alkylene oxide under loss of carbon dioxide, thereby reducing the overall yield, as indicated for instance in U.S. Pat. No. 5,510,499.

Moreover, alkylene oxide formed in this decomposition can react with residual halide-containing catalyst, thereby leading to an increased contamination of the alkylene carbonates with halogen-containing compounds. A further disadvantage resides in the fact that by treatment of alkylene carbonate with hydrotalcite, minute amounts of the corresponding alkylene glycol is produced. This alkylene glycol will however form an azeotropic mixture with the alkylene carbonate, and thus complicate the distillation, thereby leading to an increased decomposition of alkylene carbonate under the conditions of the distillation, as mentioned in U.S. Pat. No. 5,510,499.

In particular when the alkylene carbonate is further reacted with water and/or alcohol for the formation of glycol as in step (b) described above, an initial separation of alkylene carbonate from the reaction mixture would complicate the process, and reduce the overall yield of alkylene glycol.

On the other hand, in the subject process, i.e. when the product of step (a) is further subjected to step (b) as defined above, it would be expected that any halogen-containing organic compounds would be removed by hydrolysis or transesterification under the conditions usually applied. Such conditions comprise contacting the product of step (a) with water or alcohol in the presence of heterogeneous catalysts, such as stabilized magnesium oxides as for instance described in JP-A-06238165.

However, contrary to this expectation, it was found that the treatment usually applied in step (b) described above in the presence of alkylene carbonate and residual halide-containing catalyst led to an increase of the amount of organic halogen-containing compounds in the reaction mixture during the conversion of the alkylene carbonate, and did not lead to a sufficient reduction of these compounds even when continuing the reaction after the complete conversion of alkylene carbonate, at least under the conditions usually applied to avoid loss of alkylene carbonate to side reactions.

It would therefore be desirable to have a process for the preparation of alkylene glycol from alkylene carbonate, which avoids removal of the residual halide-containing catalyst at stages where this can affect the overall yield of alkylene glycol. It would likewise be desirable to be able to remove organic halogen-containing compounds without the requirement for non-aqueous conditions.

SUMMARY OF THE INVENTION

The present invention accordingly relates to a process of removing organic halogen-containing compounds from a liquid stream mainly containing one or more of the compounds selected from the group consisting of glycol, water and alcohol, which process comprises contacting at least part of the stream with an ion-exchange material containing basic anions selected from the group of hydroxide, carbonate and bicarbonate.

DETAILED DESCRIPTION OF THE INVENTION

The subject process pertains to a process wherein a liquid stream mainly comprising glycol, water and/or alcohol is submitted to a purification treatment to remove organic halogen-containing compounds. Such streams can result from a multitude of different industrial processes.

The liquid stream mainly contains one or more of the compounds selected from the group consisting of glycol, water and alcohol. In relation to the subject process the expression "mainly" means that components other than one or more compounds selected from the group consisting of glycol, water and alcohol are only present in minor amounts, preferably less than 10% by weight, more preferably less than 5% by weight, and most preferably less than 2% by weight calculated on the total of the stream.

A process that particularly results in liquid streams comprising glycols and/or water and organic halogen-containing compounds is the process for the production of glycols from alkylene oxides. This process usually includes reacting alkylene oxides with carbon dioxide under catalysis of a halide-containing catalyst to obtain alkylene carbonates and subsequently reacting the obtained alkylene carbonate with water and/or alcohol in the presence of a suitable catalyst to the corresponding glycol.

Although the removal according to the present invention can be performed at any temperature and pressure range wherein the ion-exchange material is active, for instance at or around ambient temperature, the present process preferably is performed at a temperature in the range of from 20° C. to 120° C., more preferably at a range of from 50° C. to 100° C., yet more preferably at a range of from 60° C. to 90° C., and most preferably at a range of from 75° C. to 95° C. in order to achieve a sufficiently rapid turnover for use in an industrial process. Similarly, although the removal may be performed at different pressures, it preferably is performed at a range of from 0.1 to $100*10^5$ N/m$^2$ (0.1–100 bar), more preferably at a range of from 0.5 to $20*10^5$ N/m$^2$, and most preferably at a range of from 1 to $10*10^5$ N/m$^2$.

Accordingly, the present invention preferably pertains to a process as defined above, wherein the stream containing one or more of glycol and water is produced by a process involving the steps of:
(a) reacting an alkylene oxide with carbon dioxide in the presence of a halide-containing catalyst to obtain a reaction mixture containing the corresponding alkylene carbonate,
(b) contacting the reaction mixture obtained in step (a) with water and/or alcohol in the presence of a suitable catalyst to obtain a reaction mixture containing glycol, and
(c) optionally separating at least part of the glycol formed in step (b).

In step (a) of the above process, alkylene oxide is reacted with carbon dioxide to obtain a reaction mixture containing alkylene carbonate. Preferably, the alkylene oxide has from 2 to 5 carbon atoms. Preferred alkylene oxides are ethylene oxide, propylene oxide and butylene oxide, the most preferred being ethylene oxide and propylene oxide due to the particular usefulness of their derivatives such as 1,2-ethane diol (further referred to as monoethylene glycol) and 1,2-propane diol (further referred to as monopropylene glycol), as well as di- and tri-ethylene glycol and di- and tri-propylene glycol, which are formed to a lesser extent along with the alkanediols.

Suitable catalysts for step (a) are those catalysts that promote the formation of the alkylene carbonate, and preferably include halide-containing homogeneous catalysts. Halides and/or halogen compounds according to the present invention contain one or more of the members of group VIIB of the periodic system as described on page 1–11 of the CRC Handbook of Chemistry and Physics, 72$^{nd}$ Editions, 1991. The members of this group are F, Cl, Br, I and At.

In the case of halides, the halogen atoms of the catalyst are in their anionic form. Contrary to this, in organic halogen compounds the halogen atoms are covalently bonded to a carbon atom.

Preferred halide-containing catalysts are catalysts containing bromides and iodides due to their proven reactivity in the formation of alkylene carbonates. Yet more preferred halide-containing catalysts include metal, ammonium and phosphorus containing catalysts. Phosphorus containing compounds which are suitable catalysts are phosphine compounds and phosphonium compounds. Even more preferably, the catalyst is a phosphonium catalyst, more specifically a phosphonium halide catalyst. It was found especially advantageous to employ a tetra-alkyl-phosphonium halide catalyst, more specifically a tributyl methyl phosphonium iodide due to its high stability and low level of side reactions, as well as good solvency in the reaction mixtures.

Accordingly, the present invention preferably relates to a process, wherein the halide-containing catalyst of step (a) is a phosphonium salt. The present invention also preferably relates to the subject process, wherein a halide-containing catalyst for step (a) is used which contains iodide.

The presence of such halide-containing catalysts is usually associated with the formation of halogen containing compounds along with the alkylene carbonates, as already discussed above, and catalyst degradation products. These halogen-containing compounds include inorganic halide compounds such as salts and residual catalyst as well as organic halogen containing compounds.

In the subject process, process step (a) is preferably carried out in presence of a homogeneous catalyst, and step (b) is preferably carried out in presence of a heterogeneous catalyst. More preferably, the homogeneous catalyst present in step (a) is not removed until after step (b). This has the advantage that the homogeneous catalyst of step (a) does not have to be removed under loss of alkylene carbonate.

The halogen of inorganic halide containing compounds, such as halide-containing catalyst, can be removed for instance by anion exchange with a suitable anion exchange material, as for instance described in U.S. Pat. No. 4,547,620. However, organic halogen-containing compounds, wherein the halogen is covalently bonded need to react first under loss of hydrogen halogenide or a halogen ion, which can then be removed by ion exchange. This series of reactions is therefore not an anion-exchange as described in U.S. Pat. No. 4,547,620. Organic halogen-containing compounds within the meaning of the present invention contain at least one halogen atom covalently bonded to a carbon backbone, and are usually derivatives of alkylene oxide and the halide-containing catalyst, or degradation products of the halide-containing catalyst. Accordingly, the organic halogen-containing compounds include halogenated alcohols such as vicinal 1,2-halohydrins and halogen-containing open chain and cyclic ethers, and halogenated alkyl compounds. Although many different organic halogen-containing compounds can be formed in step (a), predominant are 1,2-halohydrins such as for instance 1-iodo-2-ethanol, 1-bromo-2-ethanol, 1-chloro-2-ethanol, 1-iodo-2-propanol, 1-bromo-2-propanol and 1-chloro-2-propanol. Other halogen-containing compounds include cyclic halogen-containing ethers such as for instance iodo-methyl-dioxolane, bromo-methyl-dioxolane, chloro-methyl-dioxolane, and catalyst degradation products such as for instance methyl iodide and methyl bromide.

In the subject process, water and/or alcohol such as methanol is added in step (b) to the reaction mixture obtained in step (a). However, preferably only water is added due to the higher efficiency of the hydrolysis reaction over the transesterification, and also due to the simpler product mixture obtained.

Streams containing one or more of the group consisting of glycol, water and alcohol according to the present invention usually contain a total of less than 1% by weight of these halogen-containing compounds. Preferably, the streams contain less than 1500 ppmw of such compounds, more preferably less than 1000 ppmw, even more preferably less than 500 ppmw, again more preferably less than 400 ppmw, particularly more preferably less than 300 ppmw, and even more preferably less than 150 ppmw of halogen-containing compounds.

Depending on the halogen atom as well as on the structure of the contaminants, each of these compounds has a different reactivity, as described for instance by H. D. Cowan, C. L. McCabe and J. C. Warner, A Kinetic Study of the Neutral Hydrolysis of Ethylene Fluoro-, Bromo-, and Iodohydrin, J. Am. Chem. Soc, 1950, 72, 1194.

The present method is particularly efficient in the removal of 1,2-halohydrines. Accordingly, the subject process preferably relates to the removal of 1,2-halohydrins from streams comprising one or more of glycol, water and alcohol.

The organic halides are undesirable contaminants due to the potential environmental risks they pose. They also tend to form alkylene oxides upon exposure to heat or acidic conditions, the presence of which in the environment is also undesirable.

Furthermore, the organic halogen-containing compounds are often difficult to separate from the alkylene carbonates, alkylene oxides and even the alkylene glycols by physical separation methods such as distillation, as they may have very close boiling points and vapour pressures, and/or may form azeotropic mixtures.

Due to the above-described disadvantages associated with the presence of these compounds in the product stream of step (a), their removal is highly desirable.

After the purification treatment according to the present invention preferably at most 30 ppmw of organic halogen-containing compounds should remain in the treated stream, yet more preferably at most 15 ppmw, even more preferably at most 10 ppmw, particularly more preferably at most 5 ppmw, even more preferably at most 3 ppmw, again more preferably at most 1 ppmw, and most preferably at most 0.5 ppmw of organic halogen-containing compounds remain in the stream.

Accordingly, the subject process removes at least 70 wt % of the organic halogen-containing compounds from the treated stream, more preferably at least 85 wt %, particularly preferably at least 90 wt %, again more preferably at least 95 wt %, yet more preferably at least 99 wt %, more preferably at least 99.5 wt %, and most preferably at least 99.99 wt % of the organic halogen-containing compounds.

A suitable molar ratio of the ion exchange material to halogen-containing compounds in the subject process can be in the range of from 1 mol % to 100 mol %.

In step (b), the alkylene carbonates are submitted to a transesterification reaction with lower alcohols and/or to hydrolysis with water to obtain the corresponding 1,2-alkanediols (mono-glycols). Preferably, step (b) is performed as hydrolysis with water due to the high efficiency of this reaction, and due to the simple product mixture obtained.

Streams obtained in step (b) are essentially free from alkylene oxides. This allows performing subsequent step (c) without loss of reactive products due to side reactions described above. The streams emerging from step (b) and step (c) however may still contain all or part of the halide-containing catalyst used in step (a). Preferably, the stream obtained from step (b) is also substantially free from alkylene carbonate due to potential side reactions and to formation of additional organic halogen-containing compounds. Preferably, the stream obtained from step (b) contains less than 0.2% by weight of alkylene carbonate. More preferably the stream contains less than 0.15%, and most preferably the stream obtained from step (b) less than 0.1%, by weight of alkylene carbonate.

In optional step (c), at least part of the glycols is removed from the reaction mixture of step (b). This can be performed by separating the reaction mixture obtained in step (b) into a liquid stream and any gaseous stream containing carbon dioxide, and by further separating a stream containing glycol from the remaining stream.

Depending on the way step (c) is conducted, on the nature of the organic halogen-containing compounds and on the way the separation of the components of reaction mixture obtained in step (b) of the streams is performed, the organic halogen-containing compounds may be found in one or more of these streams. The present invention has the advantage that it can be applied to any and all of these streams, and does not require non-aqueous conditions.

In step (c), a stream containing the residual halide-containing catalyst can be separated, which may be recycled to step (a). Such a catalyst stream may also contain water and/or glycols. However, the recycle stream preferably is not submitted to the subject process, since this would lead to loss of catalyst and defeat the purpose of recycling.

Preferably, in step (c) glycol is separated from the second reaction mixture. This separation may be performed in any way known in the art. A preferred separation comprises distillation of the reaction mixture obtained in step (b), more preferably vacuum distillation, optionally followed by further distillation of one or more of the distillate or bottom streams. One or more of the fractions then separated will have a higher content of alkylene glycol, whereas others will have a high content of water. Although a relatively pure stream containing glycol and/or water can be obtained by such distillation treatment, the halogen-containing compounds present cannot be separated off without having to apply complex distillation techniques that have a very low efficiency. Therefore, such distillation is considered as not sufficiently efficient for the removal of organic halogen-containing compounds.

The streams containing glycol and/or water obtained in step (c) and preferably essentially free from catalyst may be brought in contact with the ion exchange material in any way that is known as useful to the skilled person, as for instance described for ion-exchange processes in Ullmann's Encyclopedia of Industrial Chemistry, $5^{th}$ Edition, 1989, Volume A14, pages 422 to 440. Such processes may be batch-wise or continuous processes. Preferably, the removal is conducted in a continuous process by passing at least part of a stream comprising glycols and/or water over a bed of a suitable ion-exchange material containing anions selected from the group of hydroxide, carbonate and bicarbonate. Such continuous processes have the advantage that the ion exchange material can be regenerated by ion exchange with hydroxyl, carbonate or bicarbonate anions when the content of these is exhausted by anion exchange with halogen anions. Such regenerations represent a well-known technology, and may be conducted by any suitable way.

Suitable ion-exchange materials containing basic anions selected from the group of hydroxide, carbonate and bicarbonate are inorganic or organic materials having ion-exchange properties as for instance described in Kirk-Othmer, Encyclopedia of Chemical Technology, $4^{th}$ edition, 1995, Volume 14, page 737.

A preferred embodiment of the present invention resides in the use of inorganic ion-exchange materials including hydrotalcite and hydrotalcite-like compounds containing anions selected from the group of hydroxide, carbonate and bicarbonate.

Hence, the present invention preferably relates to a process for the removal of halogen-containing compounds, wherein the ion-exchange material is a hydrotalcite-like compound. Hydrotalcite and hydrotalcite-like compounds are described for instance in the article of H. Schaper et al. in Applied Catalysis, 54, (1989) 79–90 and the article of Watanabe, Y. et al. in Microporous and Mesoporous Materials 22 (1998) 399–407. Such hydrotalcite-like compounds are composed of layered double hydroxides with the general formula:

$$[[M^{2+}xM^{3+}(OH)_{2\,(x+1)}]^+(A^{m-}{}_{1/m})^-]\cdot nH_2O$$

In this formula, $M^{2+}$ is a metal selected from the group consisting of $Mg^{2+}$, $Ca^{2+}$, $Zn^{2+}$, $Mn^{2+}$, $Ni^{2+}$, $Co^{2+}$ and $Cu^{2+}$, and $M^{3+}$ is selected from a group consisting of $Al^{3+}$, $Fe^{3+}$, and $Cr^{3+}$. Preferably due to the high stability and low side reactions, $M^{2+}$ is $Mg^{2+}$ and $M^{3+}$ is $Al^{3+}$.

In the above formula, x is a positive number and selected from the range of from 0.1 to 5, more preferably in the range of from 1 to 4, and most preferably in the range of from 2.5 to 3.5.

$A^{m-}$ represents in this formula an anion having a valence of m. Preferably $A^{m-}$ is selected from the group consisting of hydroxyl, bicarbonate and carbonate, and mixtures thereof.

In the above formula, n is a positive number in the range of from 0 to 2.0, preferably of from 0.01 to 1.0.

The structure of hydrotalcite can be visualized as positively charged octahedral metal hydroxide layers of $[M_{2+}x(OH)_{2\,(x+1)}]$, in which some of the $M^{2+}$-sites are occupied by a trivalent metal atom $M^{3+}$. These positively charged layers are separated by charge compensating, mostly hydrated, anions. Therefore, usually also water molecules are present in the hydrotalcite-like structures. Thermal treatment of the hydrotalcite-like compounds such as for instance calcination to obtain essentially water-free hydrotalcite-like material may however lead to a reduced capacity as ion-exchange material.

Naturally occurring hydrotalcite-like compounds include gahnite, hodgkinsonite, calcite, willemite, and serpentine, calcites and hydrotalcites, and usually comprise Mg and Al in a molar ratio of 3:1, together with traces of Mn and Zn. Hydrotalcite-like compounds may however also be prepared by co-precipitation methods, anion exchange in aqueous solutions, and/or any other suitable method known to a skilled person.

The use of hydrotalcite-like compounds as ion-exchange material has the advantage of low costs, and easy access to hydrotalcite-like compounds due to their well-known preparation methods. The hydrotalcite-like compounds further have the advantage of a high temperature resistance.

However, a disadvantage of hydrotalcite-like compounds is that they can form bidentate coordination complexes with glycols. Hence, metal ions of the hydrotalcite-like compounds may be dissolved from the hydrotalcite-like compounds, thereby deactivating the catalyst and contaminating the glycol stream.

In a different preferred embodiment of the present invention, another class of suitable ion-exchange materials is used, which do not have this disadvantage. These ion-exchange materials are organic anion exchange compounds, preferably anion exchange resins. Such resins generally are basic anion exchange resins having a gel structure or other structures. A further advantage of organic anion exchange resins is that they can be tailored for use and specific application, for instance by using either a gel or particles.

The resins may be based on polymers produced from styrene, divinyl benzene and acrylic monomers. Preferred are anion-exchange resins containing a matrix of crosslinked polystyrene based on copolymers of styrene and divinyl benzene. Such resins have a high mechanical and physical stability as well as a high resistance against osmotic shocks and oxygen, and good recycling potential.

The exchange of ions between the liquid and the solid ion exchange resin is controlled by the functional group attached to the resin matrix. Organic anion exchange resins have a positive fixed charge and exchange the negatively charged ions. They accordingly contain weak or strong base cations covalently bonded to the resin matrix as functional groups or functional exchange sites providing the positive fixed charge, as for instance described in Kirk-Othmer, Encyclopedia of Chemical Technology, 4$^{th}$ edition, 1995, Volume 14, pages 740–741. These functional exchange sites may be quaternary ammonium groups in the case of strong base resins, or secondary or tertiary amines in the case of weak base resins. Resins containing secondary amines however exhibited an insufficient reactivity in the subject process. Therefore, the present invention preferably relates to a process for the removal of halogen containing compounds, wherein the ion-exchange material is an organic ion exchange resin bearing quaternary amino groups.

The present process is of particular usefulness for the purification of streams comprising mono-ethylene glycol and mono-propylene glycol for the following reasons. The alkanediols are used for a range of different products, for instance as main component of coolants for liquid-cooled engines. It is therefore of particular importance that the final products are essentially free from any halogen-containing compounds, as these might lead to increased corrosion.

The present process therefore preferably relates to the removal of organic halogen-containing compounds from streams comprising mono-ethylene glycol, or from streams comprising mono-propylene glycol. Mono-propylene glycol is used widely as additive for medication, cosmetics and food. In itself it has biological acceptance. Such uses however require the absence of all potentially noxious or dangerous contaminants, in particular halogen-containing organic compounds.

The present process also relates to the removal of organic halogen-containing compounds from streams comprising di- and tri-ethylene glycol, and from streams comprising di- and tri-propylene glycol. These compounds are formed along with the corresponding alkanediols. Their use as solvents, as plasticizers and moistening agents and as building blocks for the synthesis of polyester resins, as well as carriers for fragrances also requires the absence of halogen-containing organic compounds.

Furthermore, the present invention also preferably relates to the removal of halogen-containing compounds from a stream comprising water or a mixture of glycol and water, as wastewater streams originating from industrial processes for the production of glycols usually are submitted to biotreatment. The presence of halogen-containing compounds in wastewater can however negatively affect bacteria and/or other organisms usually employed in the biotreatment.

The extent to which the halogen-containing compounds are removed from the liquid streams in the process of the present invention, can be improved further by applying the process of the present invention in combination with stripping. Stripping can be achieved by carrying out the process of the present of the invention at reduced pressure. The stripping is preferably carried out by a combination of reduced pressure and the introduction of an inert gas. The reduced pressure for stripping preferably is of from 0.01 to less than $1*10^5$ $Nm^2$, more specifically of from 0.1 to $0.9*10^5$ $N/m^2$. The inert gas for stripping can be any gas known to be suitable to someone skilled in the art. Preferably, the inert gas is nitrogen.

The process according to the present invention is further elucidated by reference to the following examples.

EXAMPLES

Example 1

2.1 ml (3.0 mmol) of AMBERJET 4200 (a crosslinked polystyrene-divinyl benzene copolymer gel-type anion exchange resin bearing trimethyl ammonium groups) in its carbonate form was filtered and washed twice with water (AMBERJET is a trademark). Then the excess of water was filtered off. The resin was then transferred to a 100 ml pressure flask equipped with a rubber septum. Then 50 ml of demineralised water containing 5 mg of 1-iodo-2-ethanol (100 ppmw or 29 mmol) were added at room temperature to the resin in the flask. The temperature was then raised to 80° C. under continuous rotation and the mixture maintained for 5 hours at this temperature.

After this period of time, the total remaining amount of 1-iodo-2-ethanol was determined by gas chromatography atomic emission detection (GC-AED), and was found to be below 1 ppmw.

Example 2

Example 1 was repeated, however employing an aqueous solution containing 100 ppmw of 1-iodo-2-propanol. After the treatment, the total amount of 1-iodo-2-propanol in the solution was found to be below 1 ppmw.

Example 3

50 ml of mono-propylene glycol containing 5.5 mg of 1-iodo-2-propanol (112 ppmw) were added to 0.25 g (0.35 mmol) of a naturally occurring uncalcined hydrotalcite containing Mg to Al in a ratio of about 3:1. After 5 hours stirring at 80° C., the solution contained less than 1 ppmw of 1-iodo-2-propanol.

Example 4

Example 3 was repeated, however using 0.25 g (0.35 mmol) of AMBERJET 4200 in its hydroxyl form. After 5 hours stirring at 80° C., the mono-propylene glycol contained less than 1 ppmw of 1-iodo-2-propanol.

Comparative Example 1

50 ml of the aqueous solution of 1-iodo-2-ethanol employed in Example 1 were heated under stirring for 5 hours at 80° C., however in absence of an ion-exchange resin. After this period of time, the solution still contained 87 ppmw of 1-iodo-2-ethanol.

Comparative Example 2

Example 3 was repeated, however using 0.75 g (0.33 mmol) of TENTAGEL —$NH_2$ (a gel-type ion exchange resins consisting of a divinyl benzene crosslinked polystyrene matrix on which an amino-functional polyethylene glycol is grafted), and 50 ml of mono-propylene glycol containing 5 mg (112 ppmw) of 1-iodo-2-ethanol (TENTAGEL is a trademark). After 5 hours stirring at 80° C., the mono-propylene glycol contained still 79 ppmw of 1-iodo-2-ethanol.

Comparative Example 3

Example 3 was repeated, however using 0.25 g (0.3 mmol) of a stabilized magnesium oxide having a ratio of Mg to Al of 10:1 as described by H. Schaper et al. in Applied Catalysis, 54, (1989) 79–90, and 50 ml of mono-propylene glycol containing 5 mg (112 ppmw) of 1-iodo-2-ethanol. Such stabilized magnesium oxide can be employed in step (b) as described above for the hydrolysis of alkylene carbonates. After 5 hours stirring at 80° C., the mono-propylene glycol contained still 31 ppmw of 1-iodo-2-ethanol.

It is clear from the above examples that organic halogen-containing compounds, in particular 1,2-halohydrins can be successfully removed by contacting streams comprising glycol and/or water with ion-exchange materials comprising basic anions selected from hydroxyl, carbonate and bicarbonate.

What is claimed is:

1. A process for removing organic halogen-containing compounds from a liquid stream mainly containing one or more of the compounds selected from the group consisting of glycol, water and alcohol, which process comprises contacting the stream with an ion-exchange material containing basic anions selected from the group of consisting of hydroxide, carbonate and bicarbonate.

2. The process of claim 1, wherein the removal is performed at a temperature in the range of from 60° C. to 100° C.

3. The process of claim 1, wherein the stream is produced by a process comprising the steps of:

(a) reacting an alkylene oxide with carbon dioxide in the presence of a halide-containing catalyst to obtain a reaction mixture containing the corresponding alkylene carbonate;

(b) contacting the reaction mixture obtained in step (a) with water and/or alcohol in the presence of a suitable catalyst to obtain a reaction mixture containing glycol; and, (c) optionally separating at least part of the glycol formed in step (b).

4. The process of claim 3, wherein the removal is performed at a temperature in the range of from 60° C. to 100° C.

5. The process of claim 3, wherein the halide-containing catalyst of step (a) is a phosphonium salt.

6. The process of claim 3, wherein the halide-containing catalyst of step (a) contains iodide.

7. The process of claim 3, wherein the halogen containing compounds are at least in part 1,2-halohydrin compounds.

8. The process of claim 3, wherein the ion-exchange material comprises a hydrotalcite-like compound.

9. The process of claim 3, wherein the ion-exchange material comprises an organic anion exchange resin bearing tertiary or quaternary amino groups.

10. The process of claim 3, wherein at least part of the stream contains monopropylene glycol.

11. The process of claim 3, wherein at least part of the stream contains monoethylene glycol.

12. The process of claim 3, wherein the halogen-containing compounds are at least in part 1,2-halohydrin compounds.

13. The process of claim 1, wherein the ion-exchange material comprises a hydrotalcite-like compound.

14. The process of claim 1, wherein the ion-exchange material comprises an organic anion exchange resin bearing tertiary or quaternary amino groups.

15. The process of claim 1, wherein at least part of the stream contains monopropylene glycol.

16. The process of claim 1, wherein at least part of the stream contains monoethylene glycol.

* * * * *